United States Patent [19]
Schneider

[11] Patent Number: 6,007,524
[45] Date of Patent: Dec. 28, 1999

[54] INCONTINENCE FLUID COLLECTION AND DISPOSAL SYSTEM

[76] Inventor: Jerome Schneider, 8355 Rednock La., Miami Lakes, Fla. 33016

[21] Appl. No.: 09/067,810

[22] Filed: Apr. 28, 1998

Related U.S. Application Data

[63] Continuation-in-part of application No. 08/683,904, Jul. 19, 1996, abandoned.

[51] Int. Cl.⁶ .............................. A61M 1/00; A61F 5/44
[52] U.S. Cl. ..................... 604/327; 604/349; 604/351; 604/347
[58] Field of Search ................... 604/327, 349, 604/351, 347

[56] References Cited

U.S. PATENT DOCUMENTS

| | | | |
|---|---|---|---|
| 4,588,397 | 5/1986 | Giacalone | 604/349 |
| 4,713,066 | 12/1987 | Komis | 604/353 |
| 5,346,483 | 9/1994 | Thaxton, Sr. | 604/353 |

Primary Examiner—John G. Weiss
Assistant Examiner—Miley C. Peppers, III

[57] ABSTRACT

An improved incontinence fluid collection and disposal system consisting of a flexible fluid reservoir assembly mounted in an opening in a reusable brief is presented. The brief is either adjustable or one piece but in either case holds the fluid reservoir assembly snugly against the body to restrict fluid leakage. An adhesive layer, normally in the form of a gasket and affixed to a flange on an inlet end of the fluid reservoir assembly, can be used to hold the fluid reservoir in position against a layer in the brief. Additional gasket layer(s) in the form of other materials can also be utilized. The fluid reservoir assembly is, in its preferred embodiment, supplied with a gelatin agent to gelatinize the urine to make for easy removal and disposal. A bactericidal agent is supplied as part of the fluid reservoir assembly to prevent infections. An optional feature is a valve in the fluid reservoir assembly to which a collection tube can be attached for long term drainage. A light vacuum can be applied to the urine collection system to assist in urine evacuation from the fluid reservoir assembly.

29 Claims, 2 Drawing Sheets

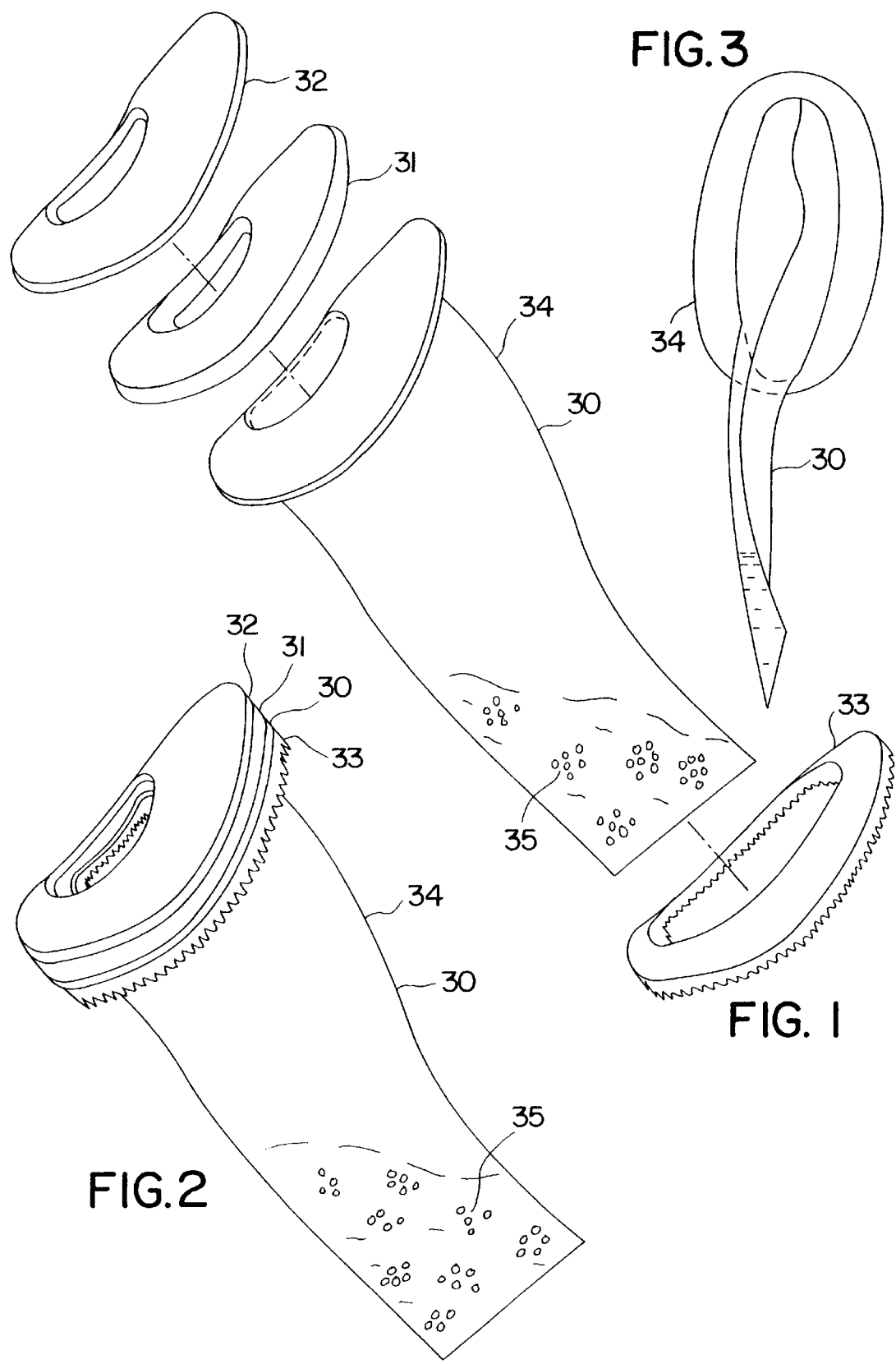

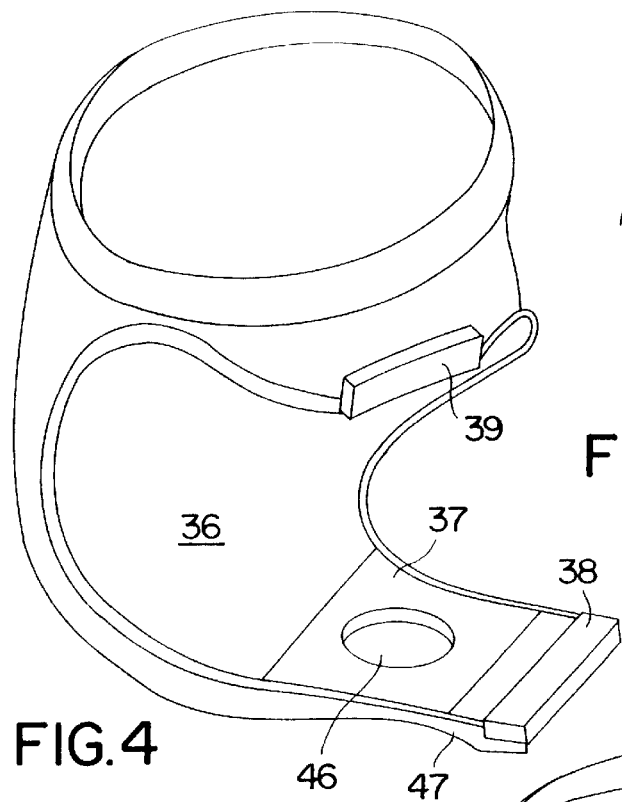
FIG. 4
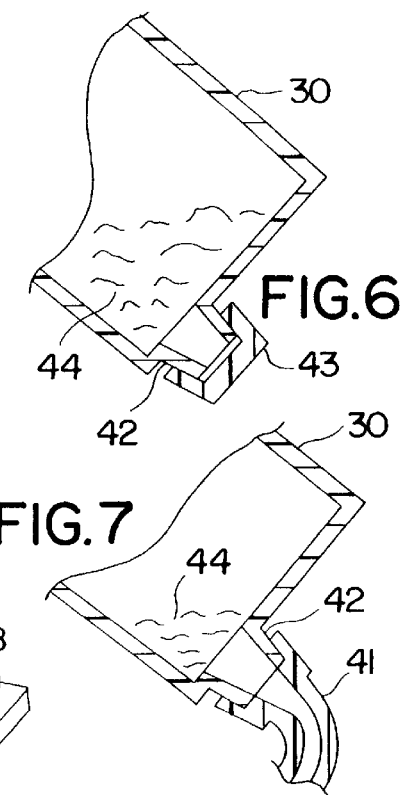
FIG. 6
FIG. 7
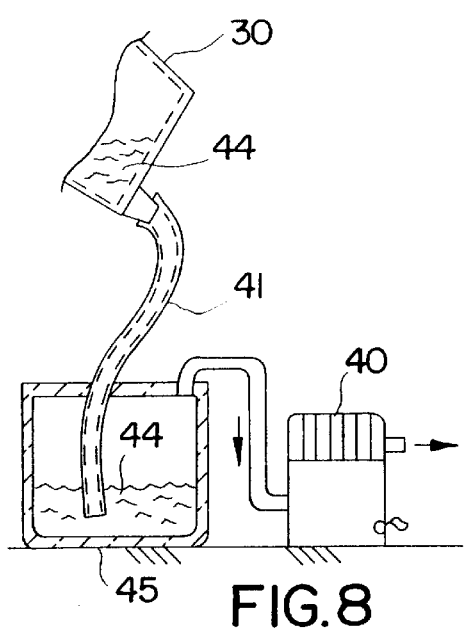
FIG. 8
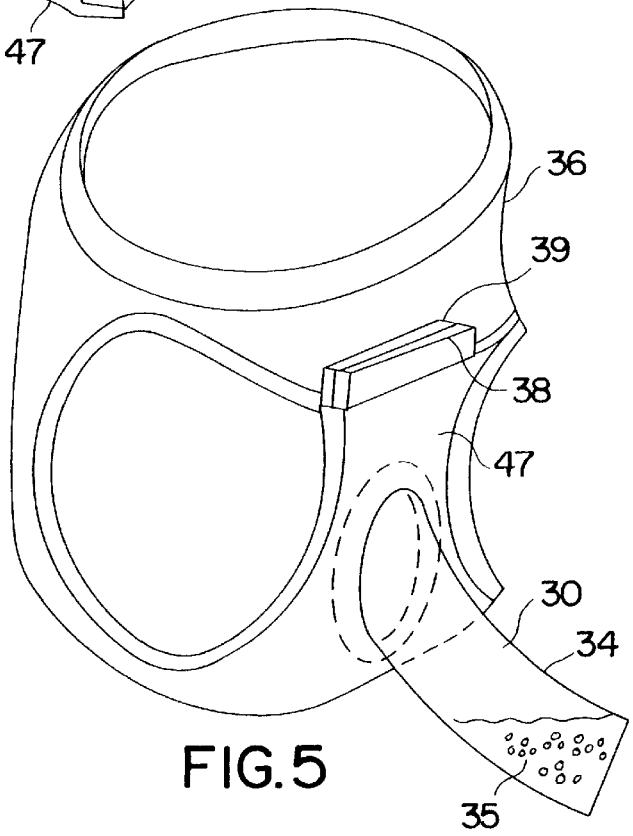
FIG. 5

INCONTINENCE FLUID COLLECTION AND DISPOSAL SYSTEM

This application is a continuation-in-part to applicant's earlier application, Ser. No. 08/683,904 filed Jul. 19, 1996 now abandoned.

BACKGROUND OF THE INVENTION

The instant invention is a new and improved means to collect and dispose of urinary incontinence fluid. For purposes of this application, it is referred to simply as an incontinence device. It is particularly applicable to older adults living in nursing homes but has application wherever urinary incontinence requires control. Existing in the marketplace are products to control urinary incontinence include a large diaper like device that is simply changed like a baby's diapers several times a day. These are rather messy and somewhat difficult to use in nursing homes and the like. Another system is offered by Hollister Incorporated, Libertyville, Ill., that consists of a long plastic pouch with a flanged inlet. The flanged inlet is actually bonded to the user's skin after shaving and cleaning around the pubic area. This makes for an uncomfortable and difficult to change and use system. The skin contacting adhesive used in the Hollister system, called the Female Urinary Incontinence Pouch, is covered by U.S. Pat. No. 4,350,785.

Applicant's instant invention incontinence device offers substantial advantages over the disposable diaper concept and the Hollister system. It does not require direct attachment to the skin and is extremely easy to use and change. It takes the form of a disposable, normally transparent plastic, collection reservoir that is inserted into a cutout in a liner in a special brief. The brief is adjustable so that it is made to hold the opening in the collection reservoir snugly against the body. The brief is easily removable with no pain or irritation to the user since there is no direct attachment to the skin.

An additive to the collection reservoir is a bactericidal agent to prevent infectious growths. Another substance that may be added to the collection reservoir is a gelation agent. This agent causes the urine to gelatinize so that it will not back up into the body cavity. The gelatinized urine is easy to dispose of along with the instant invention's reservoir.

It is also an option of the instant invention that an overnight urine collection valve can be installed in its urine collection reservoir. The urine is then, in the preferred embodiment of the invention, aspirated into a collection device. It is optionally preferred that a mild vacuum be utilized to help in this aspiration of collected urine.

SUMMARY OF THE INVENTION

With the foregoing in mind, it is the principal object of the present invention to provide a new urine incontinence collection device that is easy to install and remove with little or no discomfort to the user.

It is a related object of the invention that the incontinence device be installed in a special brief when being used.

A directly related object of the invention is that a special opening sized to fit the neck of the inventive incontinence device be provided in the brief.

A further related object of the invention is that a liner be installed in the brief proximal where the inventive incontinence device is inserted in the brief.

Yet another related object of the invention is that the brief have an adjustable body tight fit to the pubic area of the body where the inventive incontinence device is applied in order to restrict fluid leakage.

A further object of the invention is that the inventive incontinence device be formed as a long reservoir with said reservoir being, in the preferred embodiment, made of transparent plastic material.

It is a directly related object of the invention that the reservoir have a flanged opening.

Another object of the invention is that an absorbent liner gasket can be used in conjunction with the reservoir flanged opening.

A related object of the invention is that an adhesive member in the form of a gasket can be used to adhere the reservoir to the brief.

Yet another related object of the invention is that at least one additional gasket layer of selected bonding or structural material can be applied to the flanged opening of the reservoir.

An additional object of the invention is that a gelatin agent can be supplied internal to the reservoir that turns collected body fluids to a gelatin like mass.

It is a directly related object of the invention that the gelatin agent can include guar gum which is of the chemical family polysaccharide.

A further directly related object of the invention is that additives such as corn meal can be added to the guar gum to enhance the usability of the gelatin agent.

Another object of the invention is that shelf life enhancers such as methyl paraben and propyl paraben can also be added to the gelatin agent's formulation.

A further object of the invention is that the urine collection reservoir can include a bactericidal agent.

It is yet another object of the invention that the reservoir can include a fluid discharge valve that can be connected to a large volume external collection system.

A directly related object of the invention is that the external collection system can include a low level vacuum to help aspirate fluids from the reservoir.

The invention will be better understood upon reference to the drawings and detailed description of the invention which follow in which:

BRIEF DESCRIPTION OF THE DRAWINGS

FIG. 1 presents an exploded isometric view of the inventive incontinence device's urine collection reservoir showing various sealing and adhesive gaskets.

FIG. 2 is an isometric view that shows the inventive incontinence device's reservoir assembled and ready to use.

FIG. 3 is an isometric end view of the inventive incontinence device's reservoir.

FIG. 4 shows the special brief open and ready to install the inventive incontinence device's reservoir. Note the oval opening that the neck of the reservoir slips into.

FIG. 5 presents the same brief as shown in FIG. 4 but with the inventive reservoir installed and the brief closed and secure to prevent fluid leakage. Note that the user's body is not shown here for simplification.

FIG. 6 shows a valve that can optionally be installed as part of the reservoir to allow continuous drainage of the reservoir. In this instance the valve, in the form of a sealing tapered design, is sealed closed by its tapered cap.

FIG. 7 shows the same reservoir valve as presented in FIG. 6 but with the valve cap removed and a drainage collection tube installed.

FIG. 8 presents a mechanical schematic that shows a fluid collection system that is, in the preferred embodiment, vacuum assisted. This system would normally be used overnight in nursing home applications.

DETAILED DESCRIPTION OF THE FIGURES

FIG. 1 presents an exploded isometric view of the fluid collection part of inventive improved incontinence device reservoir assembly 34 which includes fluid reservoir 30, normally made from transparent plastic, bactericidal and/or gelatin agent 35, liner or gasket 31, overlay liner gasket 32 which is preferably made from a quilted layer, and adhesive gasket 33.

FIG. 2 is an isometric view that shows the improved incontinence device reservoir assembly 34 of FIG. 1 in its assembled ready to use state.

FIG. 3 is an end view of the same incontinence device reservoir assembly 34 as presented in FIG. 2.

FIG. 4 shows the brief 36 that the reservoir assembly mounts in. In this instance the brief flap 47 is open showing the opening 46 where the incontinence device is inserted. Other items shown are an adhesive pad 37 and flap adhesive strip 38 and brief upper adhesive strip 39.

FIG. 5 presents a view of the brief 36 of FIG. 4 but with the incontinence device reservoir assembly 34 installed in the opening 46 in the brief flap 47. The brief flap 47 is in its closed and ready to use position here. Note that the brief 36 is intended to be snug fitting around the body to prevent fluid leakage. Also, while a fastening brief flap 47 is illustrated here and is certainly preferred, it is not necessary that a brief flap 47 be used and a simple one piece brief, not shown, can be used so long as it has provision for mounting the incontinence device reservoir assembly 34.

FIG. 6 presents a partial cutaway view that shows an end portion of a reservoir 30 that has been modified to include a discharge nozzle or valve 42 that in this case is tapered to insure sealing against a cap 43. The fluid in the reservoir 30 is urine 44 in this illustration.

FIG. 7 presents the same partial cutaway view as FIG. 6 but with the sealing cap removed and a fluid discharge tube 41 installed. Note that other valve means, including but not limited to ball or flap valves that are not shown in order to simplify the drawings, are considered within the scope and intent of the instant invention. It is only necessary that a valve system be capable of sealing when shut and passing fluids when open.

FIG. 8 presents a schematic drawing of the incontinence device shown in part in FIG. 7 but here attached to a sealed collection beaker 45 that contains collected urine 44. Note that a very slight vacuum can be applied to the collection beaker 45 by means of a vacuum pump 40 or other vacuum generating system.

DETAILED DESCRIPTION OF THE INVENTION

The instant invention offers a new incontinence fluid collection and disposal system. The invention provides an incontinence fluid collection reservoir that is removably attached through an opening in a body fitting brief. The body fitting brief holds a flange that is part of the reservoir against the user's body such that sealing of incontinence fluids to prevent leakage is accomplished without use of adhesives that adhere to the user's skin. In its preferred embodiment, the hole in the brief is located in a flap like member that is part of the brief. To empty or change the reservoir while the user is still wearing the body fitting brief, the flap like member is detached from one end and lowered thereby exposing the lip of the reservoir which allows removal of the used reservoir. The reservoir is attached to the brief by attachment means such as an adhesive gasket material. It is preferable that the same or a similar material be also affixed to the brief adjacent to the opening so that such materials adhere to each other when in contact. The upper gasket or body contacting layer of the large opening of the fluid collection reservoir is normally made from a quilted layer of fabric that surrounds the incontinence fluid discharge opening of the user and is close fit with the user's body to prevent leakage of body fluids. It is preferable to use another layer or gasket that is made from an absorbent material between the attachment gasket and the upper or body contacting gasket. This overall method of attachment to the user's body is much more gentle than present day adhesive methods that are painful to remove, especially for older bed ridden users, as they are attached in a similar manner as adhesive bandages. Additives are generally applied to the collection reservoir to kill bacteria and/or gelatinize the incontinence fluids.

The invention further provides a way that incontinence fluids can be removed from the reservoir during long term use. To do this, the fluid reservoir, in its preferred embodiment, has a discharge valve so that incontinence fluids can be drained from the fluid reservoir as required. The procedure means that the fluid reservoir does not have to be changed during overnight usage or for other extended periods. An option an enhancement includes a separate large fluid collection container generally in the form of a beaker that is connected to the body contacting fluid reservoir by a tube. A vacuum can be applied to the collection container by a vacuum pump or other vacuum source such that the body contacting brief counted reservoir can be continually drained. This latter procedure is especially valuable for overnight applications.

While the invention has been described in connection with preferred and several alternative embodiments, it will be understood that there is no intention to thereby limit the invention. On the contrary, there is intended to be covered all alternatives, modifications and equivalents as may be included within the spirit and scope of the invention as defined by the appended claims, which are the sole definition of the invention.

What I claim is:

1. A system for collecting and disposing of body incontinence fluids, comprising:
    a fluid collecting reservoir for collecting said body incontinence fluids wherein said fluid collecting reservoir inserts into an opening in a body fitting brief,
    attachment means for attaching the fluid collecting reservoir to the body fitting brief whereby said fluid collecting reservoir can be removed for disposal,
    a bactericide agent in said fluid collecting reservoir, and
    a valve, a drain tube, and a fluid container in mechanical communication with the fluid collecting reservoir.

2. The system of claim 1, further comprising a gelatinizing agent in the fluid collecting reservoir.

3. The system of claim 2, further comprising guar gum as part of the gelatinizing agent.

4. The system of claim 2, further comprising a preservative agent as part of the gelatinizing agent.

5. The system of claim 1, further comprising a flanged inlet as part of the fluid collecting reservoir.

6. The system of claim 4, further comprising an absorbent layer gasket as part of the flanged inlet.

7. The system of claim 1, further comprising means to apply a partial vacuum to the fluid container.

8. The system of claim 1, further comprising a flap as part of said body fitting brief that is detachable at one end whereby said flap includes the opening for the fluid collecting reservoir.

9. The system of claim 8, further comprising means to adjust and attach the flap to thereby insure a snug fit.

10. A system for collecting and disposing of body incontinence fluids, comprising:

a fluid collecting reservoir for collecting said body incontinence fluids wherein said fluid collecting reservoir inserts into an opening in a body fitting brief, a gelatinizing agent in the fluid collecting reservoir, attachment means for said fluid collecting reservoir including an inlet flange and adhesive gasket, and a valve, a drain tube, and a fluid container in mechanical communication with the fluid collecting reservoir.

11. The system of claim 10, further comprising a bactericide agent in said fluid collecting reservoir.

12. The system of claim 10, further comprising guar gum as part of the gelatinizing agent.

13. The system of claim 10, further comprising a preservative agent as part of the gelatinizing agent.

14. The system of claim 10, further comprising an absorbent layer gasket as part of the flanged inlet.

15. The system of claim 10, further comprising means to apply a partial vacuum to the fluid container.

16. The system of claim 10, further comprising a flap as part of said body fitting brief that is detachable at one end whereby said flap includes the opening for the fluid collecting reservoir.

17. The system of claim 16, further comprising means to adjust and attach the flap to thereby insure a snug fit.

18. A system for collecting and disposing of body incontinence fluids, comprising:

a fluid collecting reservoir for collecting said body incontinence fluids wherein said fluid collecting reservoir inserts into an opening in a body fitting brief, attachment means including a flanged inlet and an adhesive layer gasket for attaching the fluid collecting reservoir to the body fitting brief whereby said fluid collecting reservoir can be removed for disposal, an absorbent layer in the body fitting brief;

a bactericide agent in said fluid collecting reservoir, and a valve, a drain tube, and a fluid container in mechanical communication with the fluid collecting system.

19. The system of claim 18, further comprising a gelatinizing agent in the fluid collecting reservoir.

20. The system of claim 19, further comprising guar gum as part of the gelatinizing agent.

21. The system of claim 19, further comprising a preservative agent as part of the gelatinizing agent.

22. The system of claim 18, further comprising means to apply a partial vacuum to the fluid container.

23. The system of claim 18, further comprising a flap as part of said body fitting brief that is detachable at one end whereby said flap includes the opening for the fluid collecting reservoir.

24. A system for collecting and disposing of body incontinence fluids, comprising:

a fluid collecting reservoir for collecting said body incontinence fluids wherein said fluid collecting reservoir inserts into an opening in a body fitting brief attachment means including a flanged inlet and an adhesive layer gasket for attaching the fluid collecting reservoir to the body fitting brief whereby said fluid collecting reservoir can be removed for disposal, a flap as part of said body fitting brief that is detachable at one end whereby said flap includes the opening for the fluid collecting reservoir, and a valve as part of said fluid collecting reservoir.

25. The system of claim 24, further comprising a bactericide agent in the fluid collecting reservoir.

26. The system of claim 24, further comprising a gelatinizing agent in said fluid collecting reservoir.

27. The system of claim 24, further comprising a drain tube and a fluid container in mechanical communication with the fluid collecting reservoir.

28. The system of claim 27, further comprising means to apply a partial vacuum to the fluid container.

29. The system of claim 24, further comprising an absorbent layer in the body fitting brief.

\* \* \* \* \*